(12) United States Patent
Clarysse et al.

(10) Patent No.: US 7,133,128 B2
(45) Date of Patent: Nov. 7, 2006

(54) SYSTEM AND METHOD FOR MEASURING PROPERTIES OF A SEMICONDUCTOR SUBSTRATE IN A NON-DESTRUCTIVE WAY

(75) Inventors: Trudo Clarysse, Antwerpen (BE); Wilfried Vandervorst, Mechelen (BE)

(73) Assignee: Interuniversitair Microelektronica Centrum (IMEC) vzw, Leuven (BE)

( * ) Notice: Subject to any disclaimer, the term of this patent is extended or adjusted under 35 U.S.C. 154(b) by 132 days.

(21) Appl. No.: 10/622,084

(22) Filed: Jul. 16, 2003

(65) Prior Publication Data
US 2004/0064263 A1 Apr. 1, 2004

Related U.S. Application Data

(60) Provisional application No. 60/397,566, filed on Jul. 19, 2002.

(51) Int. Cl.
*G01N 21/00* (2006.01)
*G01R 31/302* (2006.01)

(52) U.S. Cl. ............... 356/237.2; 356/432; 324/752
(58) Field of Classification Search .. 356/237.1–237.6, 356/445, 432, 502, 504, 630; 324/752, 750, 324/765
See application file for complete search history.

(56) References Cited

U.S. PATENT DOCUMENTS 5,042,952 A * 8/1991 Opsal et al. ............. 356/432
5,333,052 A * 7/1994 Finarov .................. 356/369
5,966,019 A * 10/1999 Borden ................... 324/752
6,049,220 A * 4/2000 Borden et al. ........... 324/765
6,323,951 B1 * 11/2001 Borden et al. ........... 356/502
6,392,756 B1 * 5/2002 Li et al. .................. 356/632

OTHER PUBLICATIONS

Borden, et al., "Carrier Illumination characterization of ultra-shallow implants", *Handbook of Silicon Semiconductor Metrology*, A.C. Diebold, Ed., Decker Inc., New York, pp. 97-116. (2001).
Clarysse, et al., "Carrier illumination for characterization of ultra-shallow doping profiles", as recorded in the proceeding of the Ultra-Shallow Junctions 2003 Workshop, (2003).

* cited by examiner

*Primary Examiner*—Gregory J. Toatley, Jr.
*Assistant Examiner*—Sang H. Nguyen
(74) *Attorney, Agent, or Firm*—Knobbe Martens Olson & Bear LLP

(57) ABSTRACT

One aspect of the invention discloses a method of determining the dopant profile of doped regions in a semiconductor substrate. A pump laser is used to create excess carriers in this semiconductor substrate. The excess carrier concentration will influence the reflection of a probe laser. From the reflected probe laser not only the bulk components but also the near-surface components are eliminated to only yield the bulk components.

27 Claims, 10 Drawing Sheets

SYSTEM AND METHOD FOR MEASURING PROPERTIES OF A SEMICONDUCTOR SUBSTRATE IN A NON-DESTRUCTIVE WAY

RELATED APPLICATIONS

This application claims the benefit of provisional application No. 60/397,566 filed Jul. 19, 2002, and incorporated herein by reference in its entirety.

BACKGROUND OF THE INVENTION

1. Field of the Invention

The present invention is generally related to the evaluation of semiconductor material, particularly evaluating the bulk properties of the semiconductor material.

2. Description of the Related Technology

In semiconductor processing the properties of semiconductor materials, such as Si, SiGe, GaAs, etc. . . . , and their dependence on processing conditions need to be determined. The properties of the bulk material can be changed by introducing species, e.g., by ion implantation, by annealing, e.g., Rapid Thermal processing (RTP), by manufacturing of the substrate, etc. In CMOS (Complementary Metal Oxide Silicon) devices, for example, the junction depth and profile of the source/drain regions formed in the semiconductor substrate need to be determined. To yield advanced, high-performance Complementary Metal-Oxide-Semiconductor (CMOS) technologies, it is crucial to be able to characterize quickly and reliably ultra shallow junctions. The process conditions can then be optimized to obtain the desired junction depth and profile and hence the required device characteristics.

There exist various methods to investigate the properties of the semiconductor profile. Some of these techniques are destructive, for example, spreading-resistance-profile (SRP) whereby the semiconductor substrate is cleaved along a diagonal cleavage line and a two point electrical measurement is performed at subsequent positions along this cleavage line. Some techniques are non-destructive, for example, the Carrier Illumination (CI) technique, as disclosed in U.S. Pat. Nos. 6,049,220 and 6,323,951, both hereby incorporated by reference in their entirety. For in-line monitoring of the pre- and post-anneal process steps, this Carrier Illumination™ technique has established itself as a fast, non-contact, non-destructive tool with wafer mapping capability. For process monitoring applications, the exact quantitative interpretation of the CI signal is less important as long as high repeatability and sensitivity for a particular profile or process parameter can be demonstrated.

In CI, typically, a focused "pump" laser beam (also labeled generation beam), operating at a fixed wavelength of typically 930 nm, which is larger than the band gap of the material under study, is used to generate a quasi-static excess carrier profile in the bulk of the semiconductor profile, giving rise to a depth dependent index of refraction. The excess carriers distribute themselves in the semiconductor material according to a profile which is defined as the carrier concentration (in number of carriers per cubic cm exceeding the level of carriers present within the semiconductor substrate without stimulation labeled as the background carrier concentration or profile), e.g., in the absence of illumination. This background concentration is dependent, inter alia, on the concentration of dopant atoms. Specifically, the excess carrier concentration changes from being zero outside a surface of the semiconductor material to a finite value inside the semiconductor material. This change results in a step increase in the concentration of excess carriers at the surface of the semiconductor substrate. This step increase of the excess carriers concentration at the interface between the semiconductor material under study and its surroundings, e.g., air, will be labeled as the near-surface component which will result in a near-surface component of the reflected probe beam as will be discussed later on. As the depth z, defined from the front surface into the semiconductor substrate, increases, the excess carrier concentration changes in a manner proportional, inter alia, to the change in the concentration of dopant atoms or to the presence of recombination centers. For example, in some cases, the dopant concentration rises, but in other cases the dopant concentration dips first and then rises, depending on the detailed shape of the doping profile.

The measured CI-signal is then generated by illuminating the semiconductor material with a second "probe" laser (also labeled analyzer beam), having a fixed wavelength higher than the fixed wavelength of the "pump" laser, typically 990 nm. This probe laser will be reflected at the sample surface and/or at any region with a large change in the index of refraction.

SUMMARY OF CERTAIN ASPECTS OF THE INVENTION

One aspect of the document discloses improvements over or alternatives to existing non-destructive analytical measurement techniques using optical signals, such as the Carrier Illumination™ (CI) characterization tool, as commercially available from Boxer Cross Inc. (CA, US). The sensitivity of these techniques is improved by eliminating the surface and modulated near-surface component from the measured electromagnetic signal. The sensitivity of the technique is improved by isolating the components reflected by the excess carriers within region of the active dopant profile of the substrate.

Another aspect of the invention provides a method of eliminating the near-surface component from the measured power (or amplitude and phase) of a single or multiple probe beam(s), reflected from an excess carrier depth profile created by an optionally modulated generation beam focused at the same (or near-by) wafer surface position as the probe beam(s), by variation of the probe beam configuration or/and detection characteristics.

In this aspect of the invention, two different measurements are done at different incident angles of the probe beam and by a combination of the second measurement with the first measurement, and a differential signal is obtained from which at least the near-surface component is eliminated. Alternatively, two different measurements are done at different probe laser wavelengths or frequencies (e.g., with two different lasers) and combination of both measured signals obtains a differential signal without the near-surface component. Alternatively, two different measurements are done, one for a first setting of the incident angle and wavelength of the probe laser, and the other for a second different setting of the incident angle and wavelength of the probe laser. Both measured signals are combined to obtain a differential signal without the near-surface component.

Another aspect of the invention provides a method of measuring a value of a bulk property of a semiconductor substrate, comprising providing a generation beam, providing an analyzer beam, focusing the generation beam and the analyzer beam on the semiconductor substrate, the generation beam generating in an area of the semiconductor substrate contacted by the generation beam a number of excess charge carriers, having a depth profile, the generated excess charge carriers reflecting the analyzer beam, detecting a predetermined characteristic of the reflected analyzer beam, determining the value of the bulk property from the predetermined characteristic of the reflected analyzer beam further comprising eliminating at least the near-surface contribution from the predetermined characteristic. This method further comprises focusing another analyzer beam on the area of the semiconductor substrate, detecting a predetermined characteristic of the reflected another analyzer beam, and wherein the eliminating at least the near-surface contribution comprises combining the reflected analyzer beam and the reflected another analyzer beam. In this method the analyzer beam and the another analyzer beam have a different wavelength. Also, the analyzer beam and the another analyzer beam have a different angle of incidence.

In this aspect of the invention, the probe beam is positioned at a specific angle (named the Brewster angle) such that the reflection of p-waves from the surface of the semiconductor wafer is minimized, and a p-wave polarizer is put in the reflected beam path, such that only the p-wave intensity (or amplitude and phase) of the reflected probe beam is recorded, hence eliminating any surface contribution to the measured signal.

Another aspect of the invention provides a method of measuring a value of a bulk property of a semiconductor substrate, comprising providing a generation beam, providing an analyzer beam, focusing the generation beam and the analyzer beam on the semiconductor substrate, the generation beam generating in an area of the semiconductor substrate contacted by the generation beam a number of excess charge carriers, having a depth profile, the generated excess charge carriers reflecting the analyzer beam, detecting a predetermined characteristic of the reflected analyzer beam, determining the value of the bulk property from the predetermined characteristic of the reflected analyzer beam further comprising eliminating at least the near-surface contribution from the predetermined characteristic. This method further comprises splitting the analyzer beam into a reference beam having the same wavelength, creating a difference in phase of one-eight of the same wavelength between the analyzer beam and the reference beam, and combining the reference beam and the reflected analyzer beam.

In this aspect of the invention, an additional reference beam (as described in U.S. Pat. No. 6,323,951) is used to measure the signal $P_{ref-j}$ (as defined in U.S. Pat. No. 6,323,951) with a phase change of one eight of the probe wavelength relative to the probe beam on incidence of the wafer surface.

Another aspect of the invention provides a method of measuring a value of a bulk property of a semiconductor substrate, comprising providing a generation beam, providing an analyzer beam, focusing the generation beam and the analyzer beam on the semiconductor substrate, the generation beam generating in an area of the semiconductor substrate contacted by the generation beam a number of excess charge carriers, having a depth profile, the generated excess charge carriers reflecting the analyzer beam, detecting a predetermined characteristic of the reflected analyzer beam, determining the value of the bulk property from the predetermined characteristic of the reflected analyzer beam further comprising eliminating at least the near-surface contribution from the predetermined characteristic. This method further comprises splitting the analyzer beam into a reference beam having the same wavelength, creating a difference in phase of one-eight of the same wavelength between the analyzer beam and the reference beam, and combining the reference beam and the reflected analyzer beam. This method further comprises selecting the angle of incidence of the analyzer beam so as to correspond to the Brewster angle for the semiconductor substrate of the s-component of the analyzer beam, and selecting the p-wave component of the reflected analyzer beam.

Another aspect of the invention provides an apparatus for performing the measurement of a bulk property in a region of a semiconductor substrate having a plurality of background carriers, the apparatus comprising: means for creating a plurality of excess carriers in a region of the substrate an analyzer beam of electromagnetic radiation, the analyzer beam impinging on the region of the substrate; means for detecting a predetermined characteristic of the reflected analyzer beam reflected by the plurality of excess carriers, means for determining the value of the bulk property from the predetermined characteristic of the reflected analyzer beam, wherein, the apparatus further comprises means for eliminating at least the near-surface contribution from the predetermined characteristic. This apparatus further comprises means for modulating the number of the plurality of excess carriers at a frequency that is sufficiently small to cause a majority of carriers to move out of the region to transfer by diffusion. Optionally this apparatus further comprises means for varying the wavelength and/or the angle of incidence of the analyzer beam.

In this aspect of the invention, the means for eliminating at least the near-surface contribution from the predetermined characteristic comprises another analyzer beam of electromagnetic radiation, the frequency and/or the angle of incidence of the another analyzer beam being variable.

Alternatively, the means for eliminating at least the near-surface contribution from the predetermined characteristic comprises means for tuning the angle of incidence of the analyzer beam so as to correspond to the Brewster angle for the semiconductor substrate of the s-component of the analyzer beam, and means for selecting the p-wave component of the reflected analyzer beam.

Alternatively, the means for eliminating at least the near-surface contribution from the predetermined characteristic comprises means for splitting of a reference beam from the analyzer beam, means for creating a phase difference between the reference beam and the reflected analyzer beam of one eighth of the wavelength of the analyzer beam, and means for combining the reference beam and the analyzer beam.

BRIEF DESCRIPTION OF THE DRAWINGS

All drawings are intended to illustrate some aspects and embodiments of the invention. Like numerals are used to refer to like elements.

DETAILED DESCRIPTION OF CERTAIN EMBODIMENTS OF THE INVENTION

In relation to the appended drawings the present invention is described in detail in the sequel. It is apparent, however, that a person skilled in the art can imagine several other equivalent embodiments or other ways of executing the present invention, the spirit and scope of the present invention being limited only by the terms of the appended claims.

Figure 1:
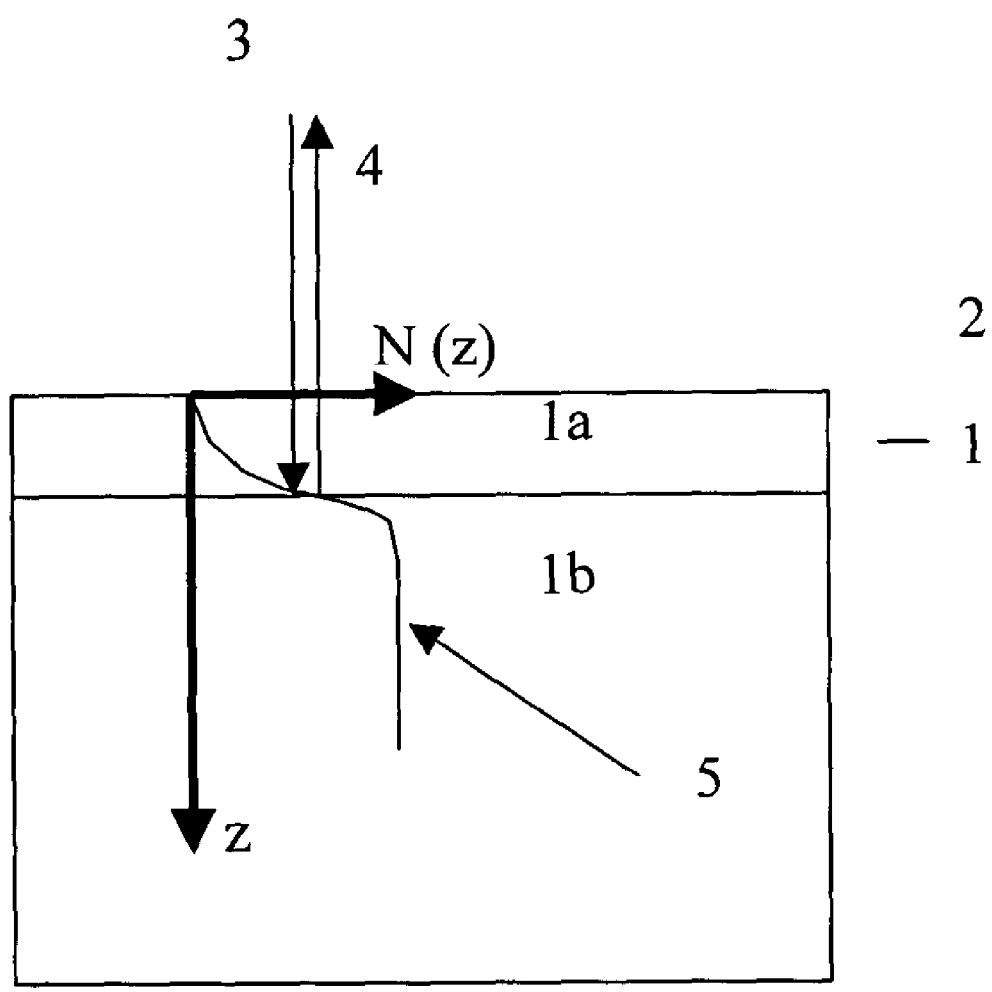
FIG. 1 illustrates a typical Carrier Illumination technique.

FIG. 1 shows a semiconductor substrate (1) and a probe laser (3) impinging from the surroundings (2) on the substrate (1). The incident (3) and reflected probe laser (4) signals are indicated by the arrows. The semiconductor substrate (1) comprises a doped layer (1a) formed on an undoped or lower doped region (1b). This substrate can be formed by depositing an in-situ doped layer, yielding a uniform doping profile over region (1a), on the layer (1b). This substrate (1) can be formed by implanting dopants into the substrate, yielding a doped region (1a) and undoped region (1b). Using ion implantation any kind of doping profile can be obtained depending on the choice of implant species, energy and dose. The layer (1a) can be doped with a dopant of the same or the opposite type of dopant used to dope the underlying layer (1b). In the substrate (1) the excess carrier profile n(z) as function of depth z into the substrate is also shown. The probe laser (3) will be reflected (4) at the various positions in this sample (1): e.g., at the surface, yielding a surface component in the reflected signal, e.g., at a change in the excess carrier profile which can occur at the surface, yielding a near-surface component or at the interface between the doped part (1a) and undoped surface on the gradient of n(z), yielding a bulk component.

The objective of the measurement is to extract from the total reflected signal the reflected probe signal originating from the bulk of the device as this signal will give information about the doping profile. The surface and the near-surface component should be eliminated from the total reflected signal. Both lasers, pump and probe lasers, are superimposed on each other and contact the semiconductor substrate (1) in the same area. Both lasers are in a fixed measurement set-up and both incident laser beams have a direction perpendicular to the wafer surface, meaning incident at a zero angle relative to the wafer surface normal. A slow modulation of the pump laser, typically at 1 kHz, is used to allow the reflection of the probe laser to be detected using phase-locked methods while maintaining quasi-static conditions. The modulation and the diffusion of the generated excess carrier in the semiconductor substrate are in phase with the modulation of the "pump" laser. The reflected probe power is given by the following theoretical formula, which is given by P. Borden, et al in, "Carrier Illumination Characterization of Ultra-Shallow Implants", in *Handbook of Silicon Semiconductor Metrology*, edited by A. C. Diebold, (Dekker Inc., New-York, 2001), 97, hereby incorporated by reference in its entirety:

$$E_r^* E_r = r_s^2 E_0^2 \left\{ 1 - \frac{\beta_n t^2}{r_s} \int_0^\infty \cos(2kn_0 z) \frac{dN(z)}{dz} dz - \frac{\beta_p t^2}{r_s} \int_0^\infty \cos(2kn_0 z) \frac{dP(z)}{dz} dz \right\} \quad (1)$$

where $E_o$ and $E_r$ are respectively the incident and reflected probe electromagnetic field, $r_s$ is the reflection coefficient at the air-Si interface (−0.549), $\beta_n$ and $\beta_p$ are negative electron- and hole-related constants which involve among other factors the electron and hole effective masses, k is the field propagation constant in vacuum, $n_0$ is the Si index of refraction in the doped region (3.435), t is the transmission coefficient at the air-Si interface and N(z) and P(z) are respectively the electron and hole excess carrier profiles. Superscript * refers to complex conjugate. The first term, i.e., 1, between the brackets corresponds to surface reflection in the absence of any carriers and is a pure DC component, meaning that it is not affected by the pump signal. The second and third term between the brackets, which follow the pump laser modulation, represent the actual CI-signal. The integral is here taken from the air-semiconductor interface into the bulk of the semiconductor substrate. From this Equation one can see that the CI signal is dominated by the derivative of the excess carrier profile. This Equation (1) can now be rewritten in the following form:

$$E_r^* E_r = r_s^2 E_0^2 \left\{ 1 - \frac{\beta_n t^2}{r_s} \left( N_{surf} + \int_{0+}^\infty \cos(2kn_{Si}z) \frac{dN(z)}{dz} dz \right) - \frac{\beta_p t^2}{r_s} \left( P_{surf} + \int_{0+}^\infty \cos(2kn_{Si}z) \frac{dP(z)}{dz} dz \right) \right\} \quad (2)$$

with $$\beta_n = -\frac{q^2}{2m_n \omega^2 \varepsilon_0 \sqrt{\varepsilon}} \quad (2b)$$

$$\beta_p = -\frac{q^2}{2m_p \omega^2 \varepsilon_0 \sqrt{\varepsilon}} \quad (2c)$$

and where $E_o$ and $E_r$ are respectively the incident and reflected probe field, $r_s$ is the reflection coefficient at the air-Si interface (−0.549), $m_n$ and $m_p$ are the electron and hole effective masses, $\omega$ is the angular frequency ($\omega = k.c$, where c is the speed of light), $k = 2\pi/\lambda$ is the field propagation constant in vacuum, $\lambda$ is the probe laser wavelength, $n_{Si}$ is the silicon index of refraction (3.435), $\epsilon_0$ and $\epsilon$ are the dielectric constants of vacuum and Silicon respectively, q is the elementary electron charge, t is the transmission coefficient at the air-Si interface, $0^+$ refers to the semiconductor side of the air-semiconductor interface, meaning that the integral is taken from immediately beneath the semiconductor surface into the bulk of the semiconductor substrate, N(z)

and P(z) are respectively the electron and hole excess carrier depth profiles, and $N_{surf}$ and $P_{surf}$ are the surface electron and hole excess carrier levels.

Equation (2) can be written as:

$$\text{power} = \text{constant}(A - [B+C] - [D-E]) \quad (3)$$

whereby:

The A-component represents the reflection of the "probe" laser at the air-semiconductor interface. This is a constant term and is independent of the modulation of the "pump" laser.

The B-component is the reflection near the surface by dopant related excess electrons. This component is modulated by the modulation of the "pump" laser. The integral ranges from 0 to $0^+$ indicating that the large value of the derivative $dN(z)/dz$ at the air-semiconductor interface is being accounted for.

The C-component represents the reflection in the bulk, meaning the reflection by excess electrons in region of the active dopant profile away from the surface. This component is modulated by the modulation of the "pump" laser. The integral ranges from $0^+$, which is just underneath the surface, into the bulk of the semiconductor material indicating that the large value of the derivative $dN(z)/dz$ at the air-semiconductor interface is not accounted for and only changes of this derivative of the excess electron profile in the bulk are taken into account.

The D-component represents the reflection near the surface by dopant related excess holes. This component is modulated by the modulation of the "pump" laser. The integral ranges from 0 to $0^+$ indicating that the large value of the derivative $dP(z)/dz$ at the air-semiconductor interface is accounted for.

The E-component represents the reflection in the bulk, meaning the reflection by excess holes in the region of the active dopant profile away from the surface. This component is modulated by the modulation of the "pump" laser. The integral ranges from $0^+$ into the bulk of the semiconductor material indicating that the large value of the derivative $dP(z)/dz$ at the air-semiconductor interface is not accounted for and only changes of this derivative in the bulk are taken into account.

Since the first term A in Equation (2), i.e., the surface reflection in the absence of any carriers, is a pure dc-component, only the second (B+C) and third (D+E) modulation-related terms, which follow the pump laser modulation, represent the actual CI-signal.

As outlined in the related technology section, the first part (B, D) of the second term (B+C) and third term (D+E) in Equations (2) and (3), involving $N_{surf}$ and $P_{surf}$, are termed the near-surface components. These near-surface components are related to the modulation of the pump-signal. It has been found by T. Clarysse et al. in "Towards a physical model for carrier illumination" internal report [2] hereby incorporated by reference in its entirety, that these near-surface components (B, D) can contribute significantly to the total signal as the peak concentration level of the dopant profile drops below $10^{20}/\text{cm}^3$. This is due to the longer Auger lifetimes for lower doping levels. Consequently, also a high CI signal is measured on lowly doped bulk substrates. The presence of the near-surface components complicates the extraction of the dopant interface or junction depth position from CI signal versus depth response curves and/or CI signal versus pump laser power curves for unknown structures, because of the significant dependence of the position of these response/power curves on the near-surface component contribution. One aspect of the invention, therefore, discloses various methods for eliminating at least the near-surface (B, D in Equations (2)–(3) term of the CI signal.

Typically CI-measurements involve the monitoring of the CI-signal as the generation power of the pump laser is swept from low to full power. The resulting curves are referred to as power curves. As the level of excess carriers will increase proportionally to the applied generation power, one might, in a simplistic view, expect a proportional increase of the CI-signal.

Figure 2:
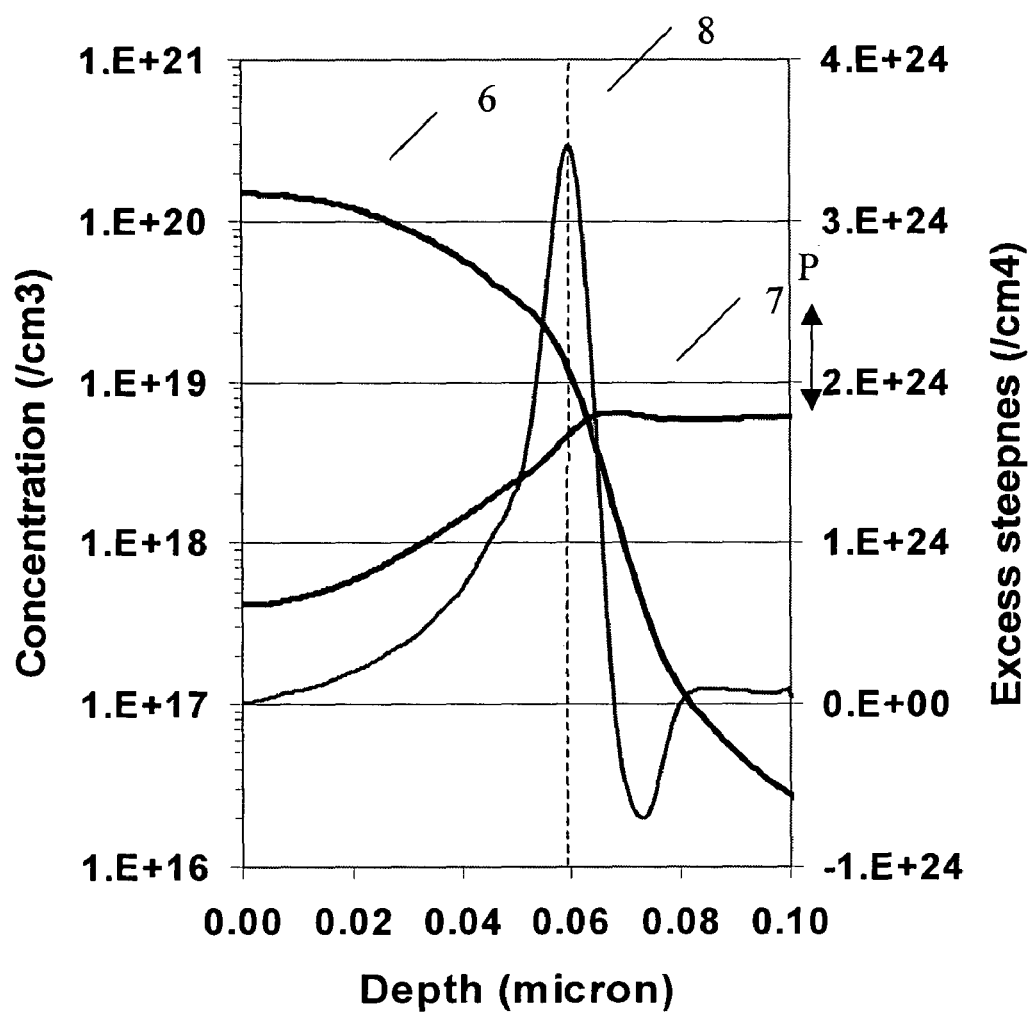
FIG. 2 illustrates dopant concentration, excess carrier concentration and derivative of the excess carrier concentration vs. depth into the substrate illustrating the interaction between excess carrier concentration and dopant profile.

FIG. 2 illustrates this mechanism: the dopant concentration (6) is plotted, the excess carrier profile (7) and the derivative of the excess carrier profile (8). As the carrier injection level increases with increasing power of the pump signal, as indicated by the arrow P in FIG. 2, one also probes different concentration levels along the slope of the dopant profile, and thus probes different profile depths, leading to a further change in the CI-signal. As such, the power curve will also contain information on the profile abruptness. This is illustrated in FIG. 3a for three different layers formed by chemical vapor deposition (CVD) as this technique allows formation of box-like profiles, as shown schematically in FIG. 3b, due to the in-situ doping of the deposited layers: a first layer (1a) is formed (55 nm thickness with constant doping level of 1e20 $\text{cm}^{-3}$, 15 nm thickness with constant doping level of 1e20 $\text{cm}^{-3}$, 17 nm thickness with constant doping level of 5e19 $\text{cm}^{-3}$) on an undoped layer (1b).

Figure 3A:
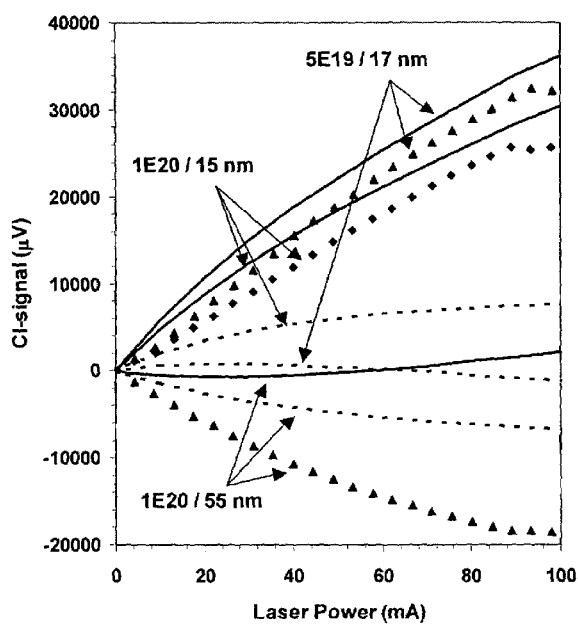
FIG. 3a illustrates experimental (symbol) versus simulated (full line) power curves for three different structures, where dashed lines illustrate the signal contribution only to the interface component.
Figure 3B:
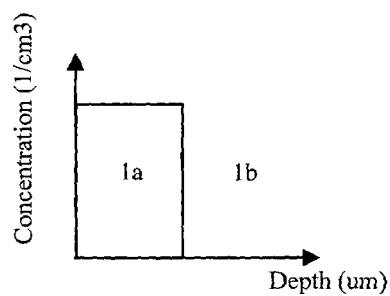
FIG. 3b illustrates experimental substrates which are formed by CVD formation an in-situ doped layer on an undoped substrate yielding a box-like doping profile.

FIG. 3a plots the experimental (symbol) versus simulated (full line) total power curves for these three structures. The nominal peak levels (in $\text{cm}^{-3}$) and interface depths are indicated for each curve. The dashed lines represent the signal contribution only due to the interface, i.e., the interface between the deposited layer (1a) and the underlying substrate (1b), component. The difference between this interface component and the total power is the surface component, which is to be eliminated. FIG. 3a shows that the impact of the surface component can adequately be simulated (within 20% at 75 mA) for two CVD layers with similar interface depths (15 and 17 nm) and different nominal peak levels ($10^{20}$ and $5 \times 10^{19}$ $\text{cm}^{-3}$). Note that the total simulated signal increases for decreasing peak levels, despite the fact that the interface signal component itself actually decreases. For deeper structures (beyond 35 nm) one can observe a significant decrease of the surface component. In the latter case the agreement between simulated and experimental power curve is, however, poor.

The excess carrier concentration is not only influenced by the dopant profile but can be also affected, e.g., by defects present in the semiconductor material under investigation. One embodiment of the invention can hence be used to eliminate the near-surface component relating to such damage or defects.

In one embodiment of the invention, two reflection measurements are performed whereby the characteristics of the "probe" laser beam are varied from one measurement to the other to eliminate the near-surface terms of the CI-signal. The results of both reflection measurements are combined in such a way that only the bulk components (C, E) in Equations (2)–(3) remain. These bulk components are representative for the properties of the semiconductor substrate such as dopant profile, generation of excess carriers, generation and recombination of carriers.

Because the "pump" signal generating the excess carriers is modulated at a low frequency, typically kHz, the surface term can be filtered out, e.g., by phase-locking, from the measured signal. As explained before the surface term (A, in Equations (2)–(3)) is not influenced by the "pump" signal.

Figure 4:
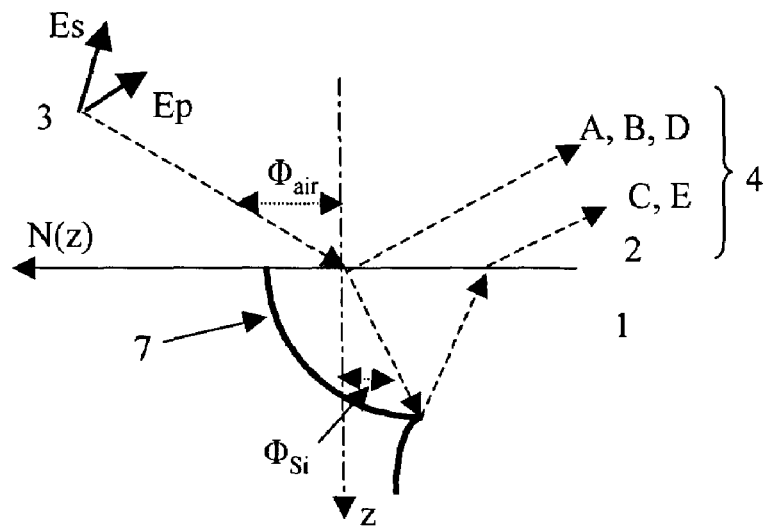
FIG. 4 illustrates probe laser beam path when incident at an angle.

In order to overcome the aforementioned limitations an extension of the CI technique is proposed which uses for the probe laser (3) beam either a controllable, variable or, adjustable incidence angle $\Phi_{air}$ (FIG. 4 for a laser beam (3) impinging the substrate (1) from the surrounding (2) and being reflected (4) at the excess carrier profile (7)), or a variable, adjustable wavelength or a combination of both. For a polarized (linearly, circular or elliptically) or unpolarized incident probe laser beam, the subsequent formulas give, in a first order approximation, the powers of the reflected field components $E_{rp}$ and $E_{rs}$ of respectively the incident p-wave (parallel to plane of incidence, see FIG. 4 or 5) $E_p$ and s-wave (perpendicular to plane of incidence, see FIG. 5) $E_s$ field components (superscript * refers to complex conjugate):

$$E_{rp}^* E_{rp} = r_{01,p}^2 E_p^* E_p \left\{ \begin{array}{l} 1 \\ -\frac{\beta_n t_{01,p} t_{10,p}}{r_{01,p} n_{Si}}(\tan^2(\phi_{Si}) - 1)\left(N_{surf} + \int_{0+}^{\infty} \cos(2kn_{Si}z\cos(\phi_{Si}))\frac{dN(z)}{dz}dz\right) \\ -\frac{\beta_p t_{01,p} t_{10,p}}{r_{01,p} n_{Si}}(\tan^2(\phi_{Si}) - 1)\left(P_{surf} + \int_{0+}^{\infty} \cos(2kn_{Si}z\cos(\phi_{Si}))\frac{dP(z)}{dz}dz\right) \end{array} \right\} \quad (4p)$$

$$E_{rs}^* E_{rs} = r_{01,s}^2 E_s^* E_s \left\{ \begin{array}{l} 1 \\ -\frac{\beta_n t_{01,s} t_{10,s}}{r_{01,s} n_{Si}} \frac{1}{\cos^2(\phi_{Si})}\left(N_{surf} + \int_{0+}^{\infty} \cos(2kn_{Si}z\cos(\phi_{Si}))\frac{dN(z)}{dz}dz\right) \\ -\frac{\beta_p t_{01,s} t_{10,s}}{r_{01,s} n_{Si}} \frac{1}{\cos^2(\phi_{Si})}\left(P_{surf} + \int_{0+}^{\infty} \cos(2kn_{Si}z\cos(\phi_{Si}))\frac{dP(z)}{dz}dz\right) \end{array} \right\} \quad (4s)$$

with $$r_{01,p}(\phi_{air}) = \frac{n_{Si}\cos(\phi_{air}) - \cos(\phi_{Si})}{n_{Si}\cos(\phi_{air}) + \cos(\phi_{Si})}, \quad r_{01,s}(\phi_{air}) = \frac{\cos(\phi_{air}) - n_{Si}\cos(\phi_{Si})}{\cos(\phi_{air}) + n_{Si}\cos(\phi_{Si})} \quad (5p, 5s)$$

$$t_{01,p}(\phi_{air}) = \frac{2\cos(\phi_{air})}{n_{Si}\cos(\phi_{air}) + \cos(\phi_{Si})}, \quad t_{01,s}(\phi_{air}) = \frac{2\cos(\phi_{air})}{\cos(\phi_{air}) + n_{Si}\cos(\phi_{Si})} \quad (6p, 6s)$$

$$t_{10,p}(\phi_{air}) = \frac{2n_{Si}\cos(\phi_{Si})}{n_{Si}\cos(\phi_{air}) + \cos(\phi_{Si})}, \quad t_{10,s}(\phi_{air}) = \frac{2n_{Si}\cos(\phi_{Si})}{\cos(\phi_{air}) + n_{Si}\cos(\phi_{Si})} \quad (6p, 6s)$$

where the incident probe beam angle $\phi_{air}$ and the refracted angle $\phi_{Si}$, as illustrated in FIG. 2a, are related by Snell's law:

$$\frac{\sin(\phi_{air})}{\sin(\phi_{Si})} = n_{Si} \quad (7)$$

and where z is the vertical depth into the wafer, indices 0 and 1 refer respectively to the air and semiconductor medium, e.g., Silicon, indices s and p refer in case of the reflection coefficient r and the transmission coefficient t respectively to s- and p-waves.

Equations (4s, 4p) can be written as:

power=constant$(A-a[B+C]-b[D-E])$ (8)

whereby:

The A-component represents the reflection of the "probe" laser at the air-semiconductor interface. This is a constant term and is independent of the modulation of the "pump" laser. This term can be filtered out, e.g., by phase-locking. This component is the surface contribution or component of the reflected "probe" beam.

The B-component represents the reflection near the surface by dopant related excess electrons. This component is modulated by the modulation of the "pump" laser. The integral ranges from 0 to $0^+$ indicating that the large value of the derivative dN(z)/dz at the air-semiconductor interface is accounted for. This component is a near-surface contribution or component of the reflected "probe" beam.

The C-component represents the reflection in the bulk, meaning the reflection by excess electrons in the active dopant profile region away from the surface. This component is modulated by the modulation of the "pump" laser. The integral ranges from $0^+$ into the bulk of the semiconductor material indicating that the large value of the derivative dN(z)/dz at the air-semiconductor interface is not accounted for and only changes of this derivative in the bulk are taken into account. This component is now dependent on the incident probe beam angle $\phi_{air}$ and the refracted angle $\phi_{Si}$. This component is a bulk contribution or component of the reflected "probe" beam.

The second term (B+C) is now function of the probe laser frequency and of the incident probe beam angle $\phi_{air}$ and the refracted angle $\phi_{Si}$ through the parameter a.

The D-component represents the reflection near the surface by dopant related excess holes. This component is modulated by the modulation of the "pump" laser. The integral ranges from 0 to $0^+$ indicating that the large value of the derivative dP(z)/dz at the air-semiconductor interface is accounted for. This component is a near-surface contribution or component of the reflected "probe" beam.

The E-component represents the reflection in the bulk, meaning the reflection by excess holes in the active dopant profile region away from the surface. This component is modulated by the modulation of the "pump" laser. The integral ranges from $0^+$ into the bulk of the semiconductor material indicating that the large value of the derivative dP(z)/dz at the air-semiconductor interface is not accounted for and only changes of this derivative in the bulk are taken into account. This component is now dependent on the incident probe beam angle $\phi_{air}$ and the refracted angle $\phi_{Si}$. This component is a bulk contribution or component of the reflected "probe" beam.

The third term (D+E) is now function of the probe laser frequency and on the incident probe beam angle $\phi_{air}$ and the refracted angles $\phi_{Si}$ through the parameter b.

The modulation-related, i.e., actually measured after filtering the first term A, part of Equations (4p) and (4s), which are the second (B+C) and third (D+E) term, can for both Equations (4s, 4p) be written in the following generic form:

$$E_{sig}(\phi_{air}, \lambda) = R(\phi_{air}, \lambda) \left( \frac{N_{surf}}{m_n} + \frac{P_{surf}}{m_p} + \int_{0+}^{\infty} \cos(2kn_{Si}z\cos(\phi_{Si})) \frac{d\left(\frac{N(z)}{m_n} + \frac{P(z)}{m_p}\right)}{dz} dz \right) \quad (9)$$

In this Equation (9) one can distinguish the near-surface terms ($N_{surf}$, $P_{surf}$) and the integral, which corresponds to the reflected signals originating from the bulk of the semiconductor material. It is important to note that the generic reflection coefficient $R(\phi_{air}, \lambda)$ in the above Equation (9) is, besides the angle of incidence $\phi_{air}$ and the probe wavelength $\lambda$, an analytical expression of known variables such as the refractive index of Silicon, the elementary charge and the dielectric constants of vacuum and Silicon. Note that the expression for the coefficient R is dependent on whether p- or s-waves are involved (see Equations (5p) and (5s)). Therefore, for any given combination of $\phi_{air}$ and $\lambda$, the coefficient $R(\phi_{air}, \lambda)$ can be determined.

Consequently a measurement of either the s-wave power, or the p-wave power at two different incidence angles or two different wavelengths (or both) of the probe beam, allows the elimination of the near surface component $$\frac{N_{surf}}{m_n} + \frac{P_{surf}}{m_p}$$

from Equation (9), by combining respectively the s or p components of both measurements, as follows:

$$E_{final} = E_{sig}(\phi_{air}^{(1)}, \lambda^{(1)}) - \frac{R(\phi_{air}^{(1)}, \lambda^{(1)})}{R(\phi_{air}^{(2)}, \lambda^{(2)})} E_{sig}(\phi_{air}^{(2)}, \lambda^{(2)}) \quad (10)$$

$$= R(\phi_{air}^{(1)}, \lambda^{(1)}) \left( \int_{0+}^{\infty} \left( \cos(2k^{(1)}n_{Si}z\cos(\phi_{Si}^{(1)})) - \cos(2k^{(2)}n_{Si}z\cos(\phi_{Si}^{(2)})) \right) \frac{d\left(\frac{N(z)}{m_n} + \frac{P(z)}{m_p}\right)}{dz} dz \right)$$

The superscripts (1) and (2) refer to the two different angles and/or wavelengths used. Hence, by using a polarization filter, to either select the p- or s-wave component of the reflected probe beam signals, it is possible, based on the approach illustrated in Equation (10), to eliminate the near-surface component completely from the final signal. One can use an unpolarized light probe laser beam incident on the surface under study and filter using a polarizor either the s or the p-component of the reflected light. One can use polarized light with a given polarization angle or polarization (circular, elliptic, linear) and filter using a polarizer either the s or the p-component of the reflected light. If only the frequency $\lambda$ of the probe laser is varied between the two measurements, both the probe laser and pump laser can be superimposed and incident orthogonal to the surface under study (see FIG. 6a).

Figure 6A:
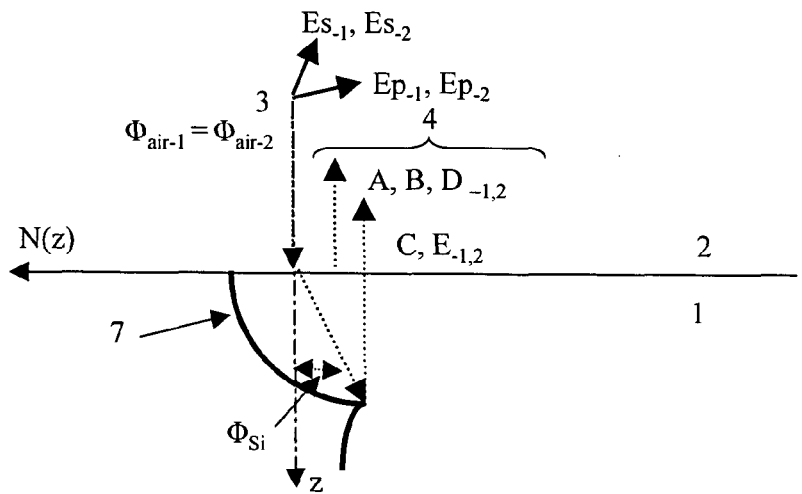
FIG. 6a illustrates probe laser beam path for two frequencies of the probe beam at the same angle.

FIG. 6a illustrates this measurement option. Both signals (subscript (1), (2)) will impinge (3) the substrate (1) in an orthogonal way. Schematically it is shown that components A, B, D of the incident signal will be reflected at the air (2)-substrate (1) interface, while the components C, E are reflected at the excess carrier profile (7). Of course all components A, B, C, D, E for each signal (subscript (1),(2)) are present in the overall reflected signal (4). In this case the s- and p-components of the incident probe laser beam would reflect for a given measurement the same way and one doesn't need to use polarized light. If the incident probe beam angle $\phi_{air}$ is varied between the two measurements then s- and p-components can reflect different and one could benefit from the use of the polarized light (see FIG. 6b).

Figure 6B:
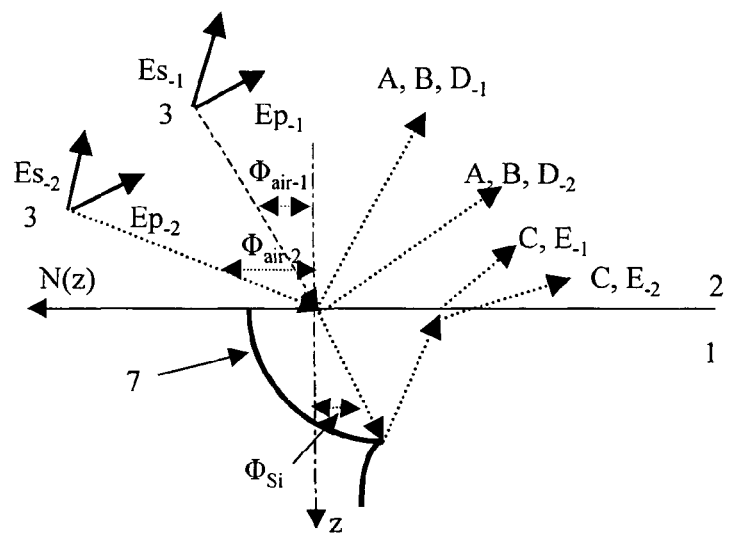
FIG. 6b illustrates probe laser beam path for two angles of incidence.

FIG. 6b illustrates this measurement option. Each input signal (subscript (1),(2)) will impinge on the substrate (1) at a different angle. For each (subscript (1),(2)) signal (3), the reflected signal (4) will contain the components A, B, C, D, E.

For example, the combination of the currently used $\lambda$=990 nm wavelength for the probe beam with a second probe beam with approximately double wavelength ($\lambda$=2 μm), is expected to give a good dynamic range dependence of the measured signal on the dopant profile depth at the carrier injection level without near-surface distortions. In this example, two distinct probe laser beams are used each operating at a different wavelength. This measurement set-up would give the largest freedom in choosing the two wavelengths. One could also use a single probe laser beam with a variable wavelength, but the range in which the wavelength of such a single laser beam could be varied might be limited.

The incident probe beam angle $\phi_{air}$ could be varied from orthogonal (0°) till about 90°. However the corresponding variation in the refracted angle $\phi_{Si}$ will depend on the semiconductor material under study as expressed by Equation (7). If the refractive index $n_{si}$ is large, then the maximum variation of $\phi_{Si}$ is limited, leading to only a small difference between the reflected signals of the two measurements. Changing the probe beam frequency $\lambda$, e.g., with a factor 2 to 4, optionally in combination with changing the incidence angle $\phi_{air}$ would result in very sensitive and accurate measurements.

Figure 7:
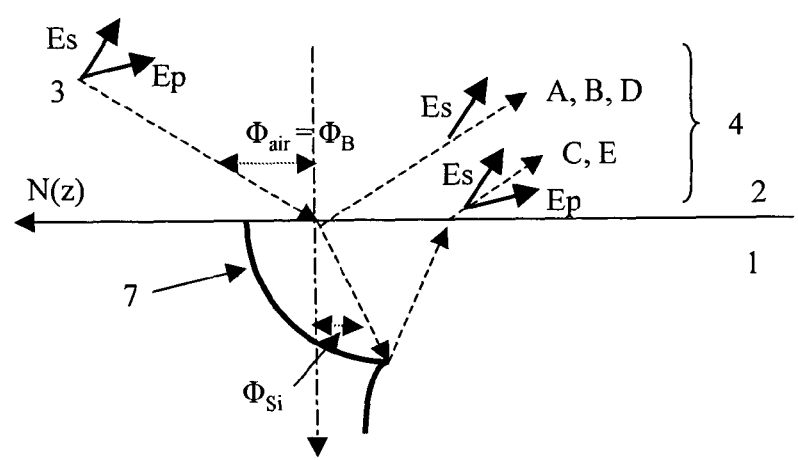
FIG. 7 illustrates probe laser beam path when impinging at the Brewster angle.

In one embodiment of the invention, only one reflection measurement is performed at a predetermined angle and at a given frequency, making use of the different reflection properties of the s- and p-component of polarized light to eliminate the near-surface term (B, D) in Equations (2)–(4). As explained above if the probe beam would impinge (3) on the surface (1) at a certain angle different from 0°, the s- and p-component would have a different reflection coefficient (see Equation (5s) and (5p)). One can further exploit this effect by using the Brewster angle for the incident probe beam. The Brewster angle $\phi_B$ is defined by:

$$\tan(\phi_B) = n_{Si}(0) \quad (11)$$

where $n_{Si}(0)$ is the refractive index of Silicon at the surface in the presence of an active dopant profile under illumination by the pump laser at a given pump power. At this angle, which is approximately 74 degrees for the transition air-to-silicon, the p-wave components of the light reflected at or near the surface would be suppressed. Hence, the light reflected at or near the surface will be almost complete s-polarized and will essentially not have a p-component. The light traveling through the wafer and reflected from within the wafer by the excess carriers in the active dopant profile region, will, however, still have a significant p- and s-component. Consequently, one can eliminate the surface and near surface contribution by placing a p-wave polarizer filter before the signal-recording unit to only withhold the p-component of the signal reflected from within the substrate. The recording unit will then only measure the parameter under study, e.g., intensity, amplitude, phase, of the p-wave light reflected from within the semiconductor wafer and no longer from the (near-) surface which is mainly s-wave as shown in FIG. 7. In this embodiment, only one measurement is performed at a predetermined angle, which is function of the semiconductor material properties. The wavelength λ of the probe signal needs not to be varied. The elimination of the surface and near-surface component is obtained by selecting the correct angle of incidence and by placing a p-wave polarizer filter in the path of the reflected light (4).

Determination of $\phi_B$ can be performed on lowly doped substrates, which are known to have the largest near surface signal from conventional CI. Changing the incidence angle $\phi_{air}$ of the probe beam until the recorded p-wave signal being zero would yield the Brewster angle for the material. It may be necessary to perform this determination of $\phi_B$ for each generation power setting of the pump beam, when measuring the recorded p-wave reflected probe beam power for different generation power settings, as the refractive index $n_{Si}(0)$ might vary with the number of excess carriers which depends on the power of the pump laser. The variation of the pump power is needed to vary the bulk excess carrier level and hence to move the depth of the position of maximum internal reflection along the active dopant profile. With the thus calibrated Brewster angle and the p-polarizer, the recorded signal on unknown wafers should only contain information from refractive index changes from within the wafer thereby excluding the near surface region, i.e., the dopant profile interface behavior of interest. Performance under these conditions may be further improved by no longer superimposing a modulation on the pump laser beam power as also the surface component (A in Equations (2)–(3)) is eliminated.

In another embodiment of the invention only one reflection measurement is performed having the probe laser beam incident orthogonal to the surface under study. A reference signal is created which has the same frequency as the incident probe laser beam and when both signals, i.e., the reference and the reflected probe signal, interfere, the near-surface components of the reflected probe signal are eliminated.

Figure 8:
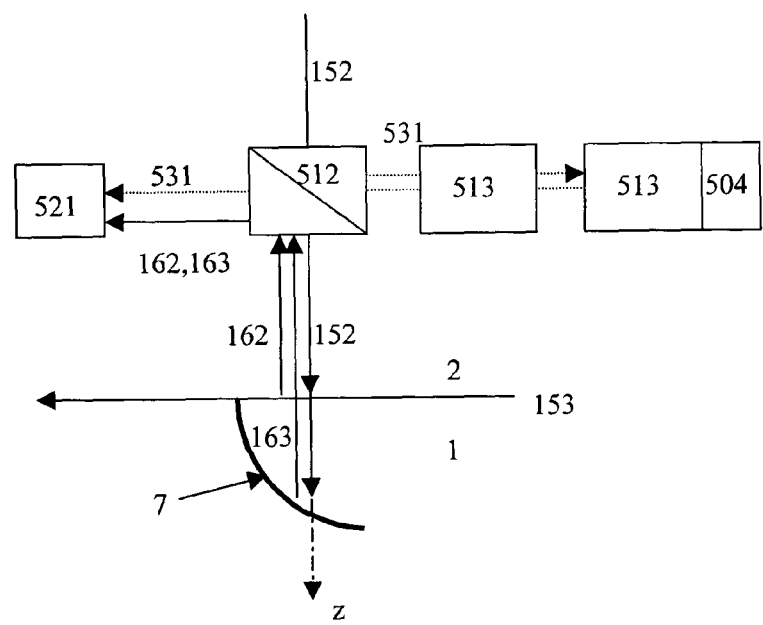
FIG. 8 illustrates probe laser beam path and reference beam path.

In U.S. Pat. No. 6,323,951 ("the '951 patent"), a system is disclosed in which an independent beam 531 is used as a reference beam, as shown in FIG. 8. Reference numeral 162 represents surface reflection. Reference numeral 504 represents a piezoelectric positioner. Reference numerals 512 and 521 represent a 50:50 beam splitter and a polarizer beam splitter, respectively. Reference numeral 513 represents a mirror. The reference beam 531 has a variable phase and polarization and is a portion of the incident probe beam 152. The reference beam 531 and the probe beam 152 have the same frequency but a different phase. The reference beam 531 can interfere with the component of the probe signal 162 reflected by the excess carrier profile at the surface, the type of interference depending on the difference in phase. The electrical field amplitude of this independent beam 531 can be written as given in formula (14) in the '951 patent as:

$$E_{ref} = E_0 e^{i2kz_{ref}} \quad (12)$$

where $z_{ref}$ is the phase angle relative to the conventional incident probe beam 152. A value $z_{ref}=0$, means that the reference beam 531 is in phase with the probe beam at the wafer surface. The measurement in this embodiment involves the recording of the signal $P_{ref-j}$ as defined in formula (16) in the '951 patent, which is reproduced here with separation of the electron and hole contributions:

$$E_r^* E_r = -\frac{\beta t^2 E_0^2}{n_{Si}} \left( \left( \frac{N_{surf}}{m_n} + \frac{P_{surf}}{m_p} \right) \cos(2kz_{ref}) + \int_{0+}^{\infty} \cos(2k(n_{Si}z - z_{ref})) \frac{d\left(\frac{N(z)}{m_n} + \frac{P(z)}{m_p}\right)}{dz} dz \right) \quad (13)$$

where $\beta = \beta_n . m_n = \beta_p . m_p$. $\beta_n$ and $\beta_p$ are negative electron- and hole-related constants which involving among other factors the electron $m_e$ and hole $m_p$ effective masses.

Figure 5:
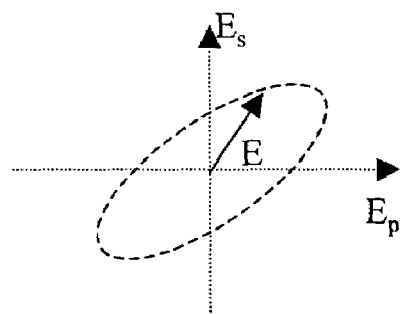
FIG. 5 illustrates the general shape of polarized incident probe laser.

Equation (12) can be written as:

$$\text{power} = \text{constant}(B+C) \quad (14)$$

whereby the term B represents the near-surface reflection by excess carriers and the term C corresponds to the reflection by excess carriers in the active dopant profile region. In this aspect of the invention the near-surface term 162 of the reflected signal can be eliminated by setting the phase difference between the incident probe signal 152 and the reference signal 153 to:

$$z_{ref} = \lambda/9 \quad (15)$$

which makes the cosine factor in the near-surface component (B) of Equation (13) zero, i.e., to use a phase change of one eight of the probe wavelength for the reference beam relative to the probe beam. FIG. 8 illustrates the measurement set-up according to this third aspect, which is a simplified version of FIG. 5 of the '951 patent. The operation of the device illustrated by FIG. 5 is disclosed in column 21, line 61 through column 24, line 30, this disclosure being incorporated by reference.

Figure 9:
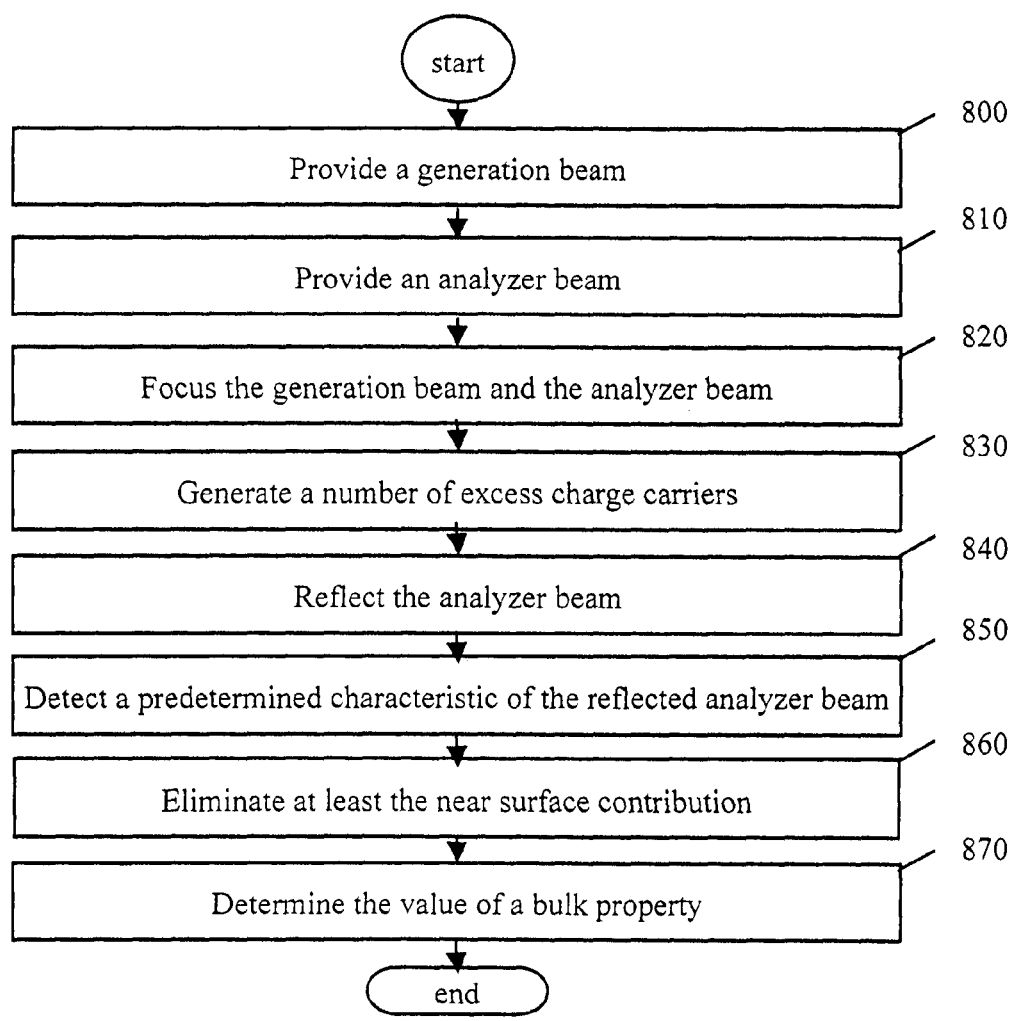
FIG. 9 illustrates a flow chart for explaining the method of measuring a bulk property of a semiconductor substrate according to one aspect of the invention.

FIG. 9 illustrates a flow chart for explaining the method of measuring a bulk property of a semiconductor substrate according to one aspect of the invention. A generation beam and an analyzer beam are provided (800, 810). The generation beam and the analyzer beam are focused on the semiconductor substrate, and the generation beam generates in an area of the semiconductor substrate contacted by the generation beam a number of excess charge carriers, having a depth profile (820, 830). The generated excess charge carriers reflect the analyzer beam (840). A predetermined characteristic (such as power, amplitude or phase) of the reflected analyzer beam is detected (850). The predetermined characteristic comprises a near-surface contribution relating to a component of the analyzer beam reflected near the surface of the semiconductor substrate. At least the near-surface contribution is eliminated from the predetermined characteristic (860). The value of a bulk property of the semiconductor substrate is determined from the predetermined characteristic of the reflected analyzer beam (870). The bulk property relates to a component of the analyzer beam reflected in an active dopant profile region away from the surface of the semiconductor substrate. This way, the bulk property of the semiconductor substrate is measured.

Figure 10:
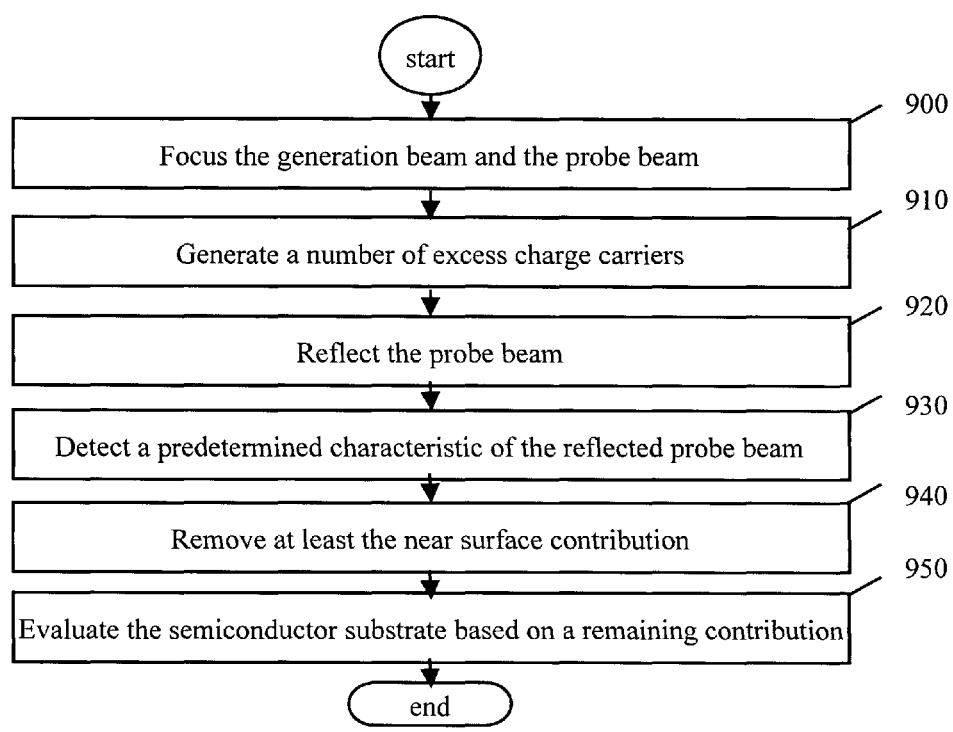
FIG. 10 illustrates a flow chart for explaining the method of evaluating a semiconductor substrate according to another aspect of the invention.

FIG. 10 illustrates a flow chart for explaining the method of evaluating a semiconductor substrate according to another aspect of the invention. A generation beam and a probe beam on the semiconductor substrate are focused in an area of the semiconductor substrate (900). The generation beam generates, in the area of the semiconductor substrate, a number of excess charge carriers, having a depth profile (910). The generated excess charge carriers reflect the probe beam (920). A predetermined characteristic (such as power, amplitude or phase) of the reflected probe beam is detected (930). The predetermined characteristic comprises a near-surface contribution relating to a component of the probe beam reflected near the surface of the semiconductor substrate. At least the near-surface contribution is removed from the predetermined characteristic (940). The semiconductor substrate is evaluated based on the remaining contribution (the bulk property), which is the predetermined characteristic from which the near-surface contribution has been removed (950).

Figure 11:
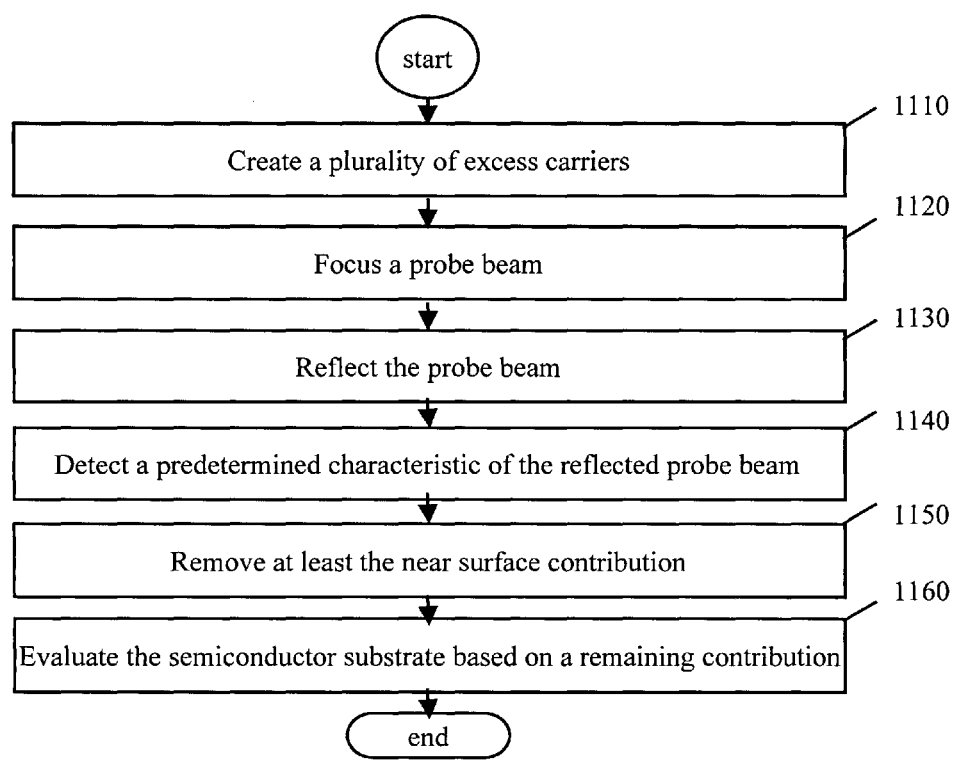
FIG. 11 illustrates a flow chart for explaining the method of evaluating a semiconductor substrate according to another aspect of the invention.

FIG. 11 illustrates a flow chart for explaining the method of evaluating a semiconductor substrate according to another aspect of the invention. A plurality of excess carriers are created in a region of the semiconductor substrate (1110). A probe beam is focused on the region of the semiconductor substrate (1120). At least part of the probe beam impinges on the region of the substrate. The plurality of excess carriers reflect the probe beam (1130). The remaining processes 1140–1160 are the same as processes 930–950 described with regard to FIG. 10.

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

What is claimed is:

1. A method of measuring a value of a bulk property of a semiconductor substrate, comprising:
   providing a generation beam;
   providing an analyzer beam;
   focusing the generation beam and the analyzer beam on the semiconductor substrate, the generation beam generating in an area of the semiconductor substrate contacted by the generation beam a number of excess charge carriers, having a depth profile, the generated excess charge carriers reflecting the analyzer beam;
   detecting a predetermined characteristic of the reflected analyzer beam, the predetermined characteristic comprising a near-surface contribution relating to a component of the analyzer beam reflected near the surface of the semiconductor substrate; and
   determining the value of the bulk property from the predetermined characteristic of the reflected analyzer beam, the bulk property relating to a component of the analyzer beam reflected in an excess carrier profile region away from the surface of the semiconductor substrate,
   wherein at least the near-surface contribution is substantially eliminated from the predetermined characteristic.

2. The method of claim 1, further comprising:
   focusing another analyzer beam on the area of the semiconductor substrate, wherein the generated excess charge carriers reflect the another analyzer beam; and
   detecting a predetermined characteristic of the reflected another analyzer beam,
   wherein the eliminating comprises combining the reflected analyzer beam and the reflected another analyzer beam.

3. The method of claim 2, wherein the analyzer beam and the another analyzer beam have a different wavelength.

4. The method of claim 3, wherein the combining the reflected analyzer beam and the reflected another analyzer beam comprises selecting either the s-wave or p-wave component of the reflected signals, the p-wave and s-wave being parallel and perpendicular components to the incident plane of the analyzer beam, respectively.

5. The method of claim 2, wherein the analyzer beam and the another analyzer beam have a different angle of incidence.

6. The method of claim 1, wherein the eliminating comprises:
   splitting the analyzer beam into a reference beam having the same wavelength as that of the analyzer beam;
   creating a difference in phase of about one-eight of the same wavelength between the analyzer beam and the reference beam; and
   combining the reference beam and the reflected analyzer beam.

7. The method of claim 1, wherein the eliminating comprises:
   selecting an incidence angle of the analyzer beam so as to correspond to the Brewster angle for the semiconductor substrate of the s-component of the analyzer beam; and
   selecting the p-wave component of the reflected analyzer beam.

8. The method of claim 7, wherein the selecting the p-wave component of the reflected analyzer beam comprises guiding the reflected analyzer beam through a p-wave polarizer.

9. The method of claim 1, wherein the bulk property is the distribution of dopants introduced in the semiconductor substrate.

10. The method of claim 1, wherein the bulk property is the defect distribution of defects present in the semiconductor substrate.

11. The method of claim 1, wherein the generation beam and the analyzer beam are focused on substantially the same area of the semiconductor substrate.

12. The method of claim 1, wherein the predetermined characteristic of the reflected analyzer beam is the power of the beam.

13. The method of claim 1, wherein the predetermined characteristic of the reflected analyzer beam is the amplitude of the beam.

14. The method of claim 1, wherein the predetermined characteristic of the reflected analyzer beam is the phase of the beam.

15. An apparatus for measuring a bulk property in a region of a semiconductor substrate having a plurality of background carriers, the apparatus comprising:
   means for creating a plurality of excess carriers in a region of the substrate;
   means for generating an analyzer beam, the analyzer beam impinging on the region of the substrate;

means for detecting a predetermined characteristic of the analyzer beam reflected by the plurality of excess carriers; and means for determining the value of the bulk property from the predetermined characteristic of the reflected analyzer beam, means for substantially eliminating at least the near-surface contribution from the predetermined characteristic.

16. The apparatus of claim 15, further comprising means for modulating the number of the plurality of excess carriers at a frequency that is sufficiently small to cause a majority of carriers moving out of the region to transfer by diffusion.

17. The apparatus of claim 16, further comprising means for varying the wavelength and/or the angle of incidence of the analyzer beam.

18. The apparatus of claim 16, wherein the means for eliminating comprises:
means for generating another analyzer beam, the frequency and/or the angle of incidence of the another analyzer beam being variable.

19. The apparatus of claim 15, wherein the means for eliminating comprises:
means for tuning the angle of incidence of the analyzer beam so as to correspond to the Brewster angle for the semiconductor substrate of the s-component of the analyzer beam; and
means for selecting the p-wave component of the reflected analyzer beam.

20. The apparatus of claim 15, wherein the means for eliminating comprises:
means for splitting a reference beam from the analyzer beam;
means for creating a phase difference between the reference beam and the reflected analyzer beam of about one eighth of the wavelength of the analyzer beam; and
means for combining the reference beam and the analyzer beam.

21. A method of evaluating a semiconductor substrate, comprising:
focusing a generation beam and a probe beam on the semiconductor substrate, the generation beam generating, in an area of the semiconductor substrate focused by the generation beam, a number of excess charge carriers, having a depth profile, the generated excess charge carriers reflecting the probe beam;
detecting a predetermined characteristic of the reflected probe beam, the predetermined characteristic comprising a near-surface contribution relating to a component of the probe beam reflected near the surface of the semiconductor substrate; and
substantially removing at least the near-surface contribution from the predetermined characteristic.

22. The method of claim 21, wherein the predetermined characteristic comprises at least one of the following: the power of the reflected probe beam, the amplitude of the reflected probe beam, or the phase of the reflected probe beam.

23. The method of claim 21, further comprising determining a value of a bulk property of the semiconductor substrate based on the predetermined characteristic from which the near-surface contribution has been removed, the bulk property relating to a component of the probe beam reflected in an access carrier profile region away from the surface of the semiconductor substrate.

24. A method of evaluating a semiconductor substrate having a plurality of background carriers, the method comprising:
creating a plurality of excess carriers in a region of the semiconductor substrate;
focusing a probe beam on the region of the semiconductor substrate, the plurality of excess carriers reflecting the probe beam, at least part of the probe beam impinging on the region of the substrate;
detecting a predetermined characteristic of the reflected probe beam, the predetermined characteristic comprising a near-surface contribution relating to a component of the probe beam reflected near the surface of the semiconductor substrate; and
substantially removing at least the near-surface contribution from the predetermined characteristic.

25. The method of claim 24, further comprising determining a value of a bulk property of the semiconductor substrate based on the predetermined characteristic from which the near-surface contribution has been removed, the bulk property relating to a component of the probe beam reflected in an access carrier profile region away from the surface of the semiconductor substrate.

26. An apparatus for measuring a value of a bulk property of a semiconductor substrate, comprising:
means for providing a generation beam;
means for providing an analyzer beam;
means for focusing the generation beam and the analyzer beam on the semiconductor substrate, the generation beam generating in an area of the semiconductor substrate contacted by the generation beam a number of excess charge carriers, having a depth profile, the generated excess charge carriers reflecting the analyzer beam;
means for detecting a predetermined characteristic of the reflected analyzer beam, the predetermined characteristic comprising a near-surface contribution relating to a component of the analyzer beam reflected near the surface of the semiconductor substrate; and
means for determining the value of the bulk property from the predetermined characteristic of the reflected analyzer beam, the bulk property relating to a component of the analyzer beam reflected in an excess carrier profile region away from the surface of the semiconductor substrate,
wherein at least the near-surface contribution is substantially eliminated from the predetermined characteristic.

27. An apparatus for evaluating a semiconductor substrate, comprising:
means for focusing a generation beam and a probe beam on the semiconductor substrate, the generation beam generating, in an area of the semiconductor substrate focused by the generation beam, a number of excess charge carriers, having a depth profile, the generated excess charge carriers reflecting the probe beam;
means for detecting a predetermined characteristic of the reflected probe beam, the predetermined characteristic comprising a near-surface contribution relating to a component of the probe beam reflected near the surface of the semiconductor substrate; and
means for substantially removing at least the near-surface contribution from the predetermined characteristic.

* * * * *